(12) United States Patent
Takada et al.

(10) Patent No.: US 6,190,702 B1
(45) Date of Patent: *Feb. 20, 2001

(54) SUSTAINED-RELEASED MATERIAL PREPARED BY DISPERSING A LYOPHILIZED POLYPEPTIDE IN AN OIL PHASE

(75) Inventors: Shigeyuki Takada, Kobe; Tomofumi Kurokawa, Kawabe-gun; Susumu Iwasa, Tsuzuki-gun, all of (JP)

(73) Assignee: Takeda Chemical Industries, Ltd., Osaka (JP)

( * ) Notice: This patent issued on a continued prosecution application filed under 37 CFR 1.53(d), and is subject to the twenty year patent term provisions of 35 U.S.C. 154(a)(2).

Under 35 U.S.C. 154(b), the term of this patent shall be extended for 0 days.

(21) Appl. No.: 08/849,172
(22) PCT Filed: Mar. 27, 1997
(86) PCT No.: PCT/JP97/01041
 § 371 Date: May 30, 1998
 § 102(e) Date: May 30, 1998
(87) PCT Pub. No.: WO97/35563
 PCT Pub. Date: Oct. 2, 1997

(30) Foreign Application Priority Data

Mar. 28, 1996 (JP) .................................................. 8-073016

(51) Int. Cl.[7] ................................ A61K 9/50; A61K 9/52; A61K 9/16
(52) U.S. Cl. ........................ 424/501; 424/489; 424/499; 424/451; 424/457; 514/963; 514/964
(58) Field of Search ................................ 424/489, 426, 424/451, 457, 499, 501; 514/963, 964

(56) References Cited

U.S. PATENT DOCUMENTS

| | | | |
|---|---|---|---|
| 4,774,091 | 9/1988 | Yamahira et al. | 424/426 |
| 4,962,091 | 10/1990 | Eppstein et al. | 514/2 |
| 4,963,367 | 10/1990 | Ecanow | 424/485 |
| 5,021,241 | 6/1991 | Yamahira et al. | 424/426 |
| 5,288,502 | 2/1994 | McGinity et al. | 424/484 |
| 5,385,738 | 1/1995 | Yamahira et al. | 424/489 |
| 5,876,756 | * 3/1999 | Takada et al. | |
| 6,045,830 | * 4/2000 | Igari et al. | |

FOREIGN PATENT DOCUMENTS

| | | |
|---|---|---|
| 0461630 | 12/1991 | (EP) . |
| 0 481 732 A1 | * 4/1992 | (EP) . |
| 0633020 | 1/1995 | (EP) . |
| 0 709 085 A1 | * 5/1996 | (EP) . |
| 5-112468 | 7/1993 | (JP) . |
| 12158 | 6/1994 | (WO) . |
| 19020 | 9/1994 | (WO) . |
| 94/19020 | * 9/1994 | (WO) . |
| 11009 | 4/1995 | (WO) . |

OTHER PUBLICATIONS

M–K. Yeh et al., Journal of Controlled Release, vol. 33 (1995) 437–445.
Hayashi et al., Pharmaceutical Research, vol. 11, No. 2 (1994) 337–340.
T.G. Park et al., Pharmaceutical Research, vol. 9, No. 1 (1992) 37–39.

* cited by examiner

Primary Examiner—Thurman K. Page
Assistant Examiner—Brian K. Seidleck
(74) Attorney, Agent, or Firm—Fitzpatrick, Cella, Harper & Scinto

(57) ABSTRACT

A sustained-release preparation containing a bioactive polypeptide is prepared using a starting material containing a lyophilized product of an aqueous solution or suspension of the bioactive polypeptide in a non-ionic surfactant. The lyophilized product is dispersed in an oil phase, which further contains a biocompatible, biodegradable polymer.

33 Claims, 3 Drawing Sheets

SUSTAINED-RELEASED MATERIAL PREPARED BY DISPERSING A LYOPHILIZED POLYPEPTIDE IN AN OIL PHASE

This application is a 371 of PCT/JP97/01041, filed Mar. 27, 1997.

BACKGROUND OF THE INVENTION

1. Field of the Invention

The present invention relates to a sustained-release preparation suited for sustained release of a bioactive polypeptide and a method of producing the sustained-release preparation.

2. Brief Description of the Background Art

Bioactive polypeptides or derivatives thereof are known to exhibit various pharmacological actions in vivo. As the recent advances in gene or cell engineering have enabled their production at high purity and in large amounts, an increased number of such substances have been brought into clinical application as pharmaceuticals. When orally administered, however, these bioactive polypeptides are readily decomposed by enzymes in the gastrointestinal tract, resulting in very low absorption rates. Also, many of them are short in biological half-life. For these reasons, repetitive intramuscular or subcutaneous injection or intravenous drip infusion is normally used to administer them. Although these methods are acceptable when administration frequency is limited to a few times, frequent administration in chronic diseases poses an extreme burden on the patient's body. For example, interferon a (IFNα) is given to patients with hepatitis C on consecutive days for 4 weeks or more, and growth hormone is given to infant or young patients with pituitary dwarfism by subcutaneous or intramuscular administration consecutive days or every two days for an extended period of time from several months to 10 years or more. In addition, to achieve symptom remission, complete healing or linear growth in these diseases, it is reportedly necessary to maintain clinically useful levels of active ingredients for an extended period of time. To solve this problem, there have been a large number of attempts to develop sustained-release preparations containing a bioactive polypeptide [Clinical Reviews in Therapeutic Drug Carrier Systems, No. 12, pp. 1–99 (1995)].

WO94/19020 discloses a method of polypeptide stabilization by dissolving a mixture of polypeptide and polyol in an organic solvent. W094/12158 discloses a sustained-release preparation obtained by adding a mixture of polymer and growth hormone to an organic solvent. EPA 251476 (U.S. Pat. No. 4962091, Japanese Patent Unexamined Publication No. 2930/1988) discloses a matrix comprising a polypeptide dispersed in polylactide. Japanese Patent Unexamined Publication Nos. 46116/1992 and 65063/1994 disclose a method of producing a sustained-release preparation by dissolving a biodegradable polymer and a fatty acid salt in an organic solvent and prepared as an o/w emulsion. Japanese Patent Examined Publication No. 57658/1994 discloses a sustained-release preparation comprising a bioactive polypeptide uniformly contained in a carrier consisting of atherocollagen or the mixture of atherocollagen and gelatin. Pharmaceutical Research, Vol. 9, No. 1, pp. 37–39 (1992), Pharmaceutical Research, Vol. 11, No. 2, pp. 337–340 (1994) and the Journal of Controlled Release, Vol. 33, pp. 437–445 (1995) disclose a sustained-release preparation of bioactive polypeptide from a w/o/w/emulsion obtained by adding the polypeptide to a mixed solution of a surfactant and a polymer in an organic solvent. As stated above, most prior art methods are based on the w/o/w method wherein a surfactant, if used, and a biodegradable polymer are dissolved in an organic solvent, and an aqueous solution of a bioactive polypeptide is added to the resulting oil phase. The s/o/w method has also been reported wherein a powdered bioactive polypeptide is added directly to an oil phase containing a biodegradable polymer and, if used, a surfactant. However, all these methods fail to provide clinically practical pharmaceuticals, since decreased stability of the bioactive polypeptide significantly affects recovery rates or lowers the quality of the sustained-release preparation obtained.

Although there have been reported various attempts to produce a sustained-release preparation, while retaining the bioactivity of a bioactive polypeptide, as stated above, there have been no preparations that are clinically satisfactory in terms of the ratio of bioactive polypeptide entrapped in biocompatible polymer, suppression of initial release, long and constant sustained-release property except some preparations of LH-RH analogs and so on. Specifically, in preparations of bioactive polypeptides having higher structure, sufficient yields or pharmacological effects have not been obtained because the blood drug concentration is unexpectedly high in the initial stage after administration, because the drug release rate is not constant during the sustained-release period, or because the bioactive polypeptide is denatured during the manufacturing process. Also, in the case of sustained-release indwellable preparations, other problems arise, i.e., full compliance cannot be obtained due to pain at administration site, and the heterozoic collagen for base may be antigenic.

Thus, there is demand for the development of a clinically useful sustained-release preparation exhibiting long and constant sustained-release, while retaining the bioactivity of a bioactive polypeptide, and a method of its production.

SUMMARY OF THE INVENTION

The present inventors made extensive investigation to solve the above problems, and unexpectedly found that an excellent sustained-release preparation with an improved entrapment ratio of bioactive polypeptide in polymer, dramatically suppressed initial release, and a long and constant release rate can be obtained by mixing a bioactive polypeptide and a surfactant, rapidly drying the mixture, dispersing the resulting fine particles in an oil phase, and subsequently shaping the dispersion into a sustained-release preparation. The present inventors made further investigation based on this finding, and developed the present invention.

Accordingly, the present invention relates to: (1) a method of producing a sustained-release preparation, which comprises dispersing a rapidly dried product containing a bioactive polypeptide and a surfactant in an oil phase, followed by shaping the resulting dispersion; (2) the production method of term (1) above, wherein the average particle diameter of the rapidly dried product dispersed in the oil phase is about 0.05 $\mu$m to about 50 $\mu$m; (3) the production method of term (1) above, wherein the ratio by weight of the bioactive polypeptide and the surfactant is about 1:0.001 to about 1:1,000; (4) the production method of term (1) above, wherein the oil phase is an organic solvent phase containing a biocompatible polymer; (5) the production method of term (4) above, wherein the biocompatible polymer concentration in the organic solvent is about 0.01% (w/w) to about 80% (w/w); (6) the production method of term (4) above, wherein the ratio of surfactant used to the total amount of bioactive polypeptide, surfactant and biocompatible polymer is about 0.002% (w/w) to about 50% (w/w); (7) the production method of term (1) above, wherein the bioactive polypeptide is soluble in water; (8) the production method of term (1) above, wherein the bioactive polypeptide is a hormone; (9) the production method of term (8) above, wherein the hormone is a growth hormone; (10) the production method of term (8) above, wherein the hormone is an insulin; (11) the production method of term (1) above, wherein the bioactive polypeptide is a cytokine; (12) the production method of term (11) above, wherein the cytokine is an interferon or interleukin; (13) the production method of term (4) above, wherein the biocompatible polymer is a biodegradable polymer; (14) the production method of term (13) above, wherein the biodegradable polymer is a fatty acid polyester; (15) the production method of term (14) above, wherein the fatty acid polyester is a lactic acid-glycolic acid copolymer; (16) the production method of term (14) above, wherein the molecular weight of the lactic acid-glycolic acid copolymer is about 3,000 to 70,000 and the lactic acid/glycolic acid content ratio is about 100/0 to about 30/70; (17) the production method of term (14) above, wherein the fatty acid polyester is a hydroxybutyric acid-glycolic acid copolymer; (18) the production method of term (17) above, wherein the molecular weight of the hydroxy-butyric acid-glycolic acid copolymer is about 3,000 to about 70,000 and the hydroxybutyric acid/glycolic acid content ratio is about 100/0 to about 40/60; (19) the production method of term (1) above, wherein the surfactant is non-ionic; (20) the production method of term (19) above, wherein the hydrophile/lipophile balance (HLB) of the non-ionic surfactant is not less than 10; (21) the production method of term (1) above, wherein the surfactant comprises 1 or more nonionic surfactants selected from the group consisting of polyoxyethylene-polyoxypropylene copolymer, polyoxyethylene hydrogenated castor oil, polyoxyethylene alkyl ether and polyvinylpyrrolidone; (22) the production method of term (19) above, wherein the non-ionic surfactant is polyoxyethylene-polyoxypropylene copolymer; (23) the production method of term (1) above, wherein the sustained-release preparation is a microcapsule; (24) the production method of term (23) above, wherein the average particle diameter of the microcapsule is about 1.0 to about 200 µm; (25) the production method of term (1) above, wherein the sustained-release preparation is an injectable preparation; (26) a dispersion of a rapidly dried product containing a bioactive polypeptide and a surfactant in an oil phase; (27) the dispersion of term (26) above, wherein the average particle diameter of the rapidly dried product dispersed in the oil phase is about 0.05 µm to 50 µm; (28) a starting material for sustained-release preparation comprising a rapidly dried product of an aqueous solution or suspension containing a bioactive polypeptide and a surfactant dispersed in an oil phase containing a biocompatible polymer, (29) a sustained-release preparation for pharmaceutical use produced by the production method of term (1) above, (30) a sustained-release preparation of term (29), wherein the bioactive polypeptide is a growth hormone, and (31) a medicament for treatment or prevention of growth hormone deficiency, Turnerts syndrome, pituitary dwarfism, chronic renal disease, achondroplasia, adult hypopituitarism, Down syndrome, Silver syndrome, hypochondroplasia, osteoporosis and juvenile chronic arthritis, which comprises the sustained-release preparation of term (30).

DETAILED DESCRIPTION OF THE INVENTION

Figure 1:
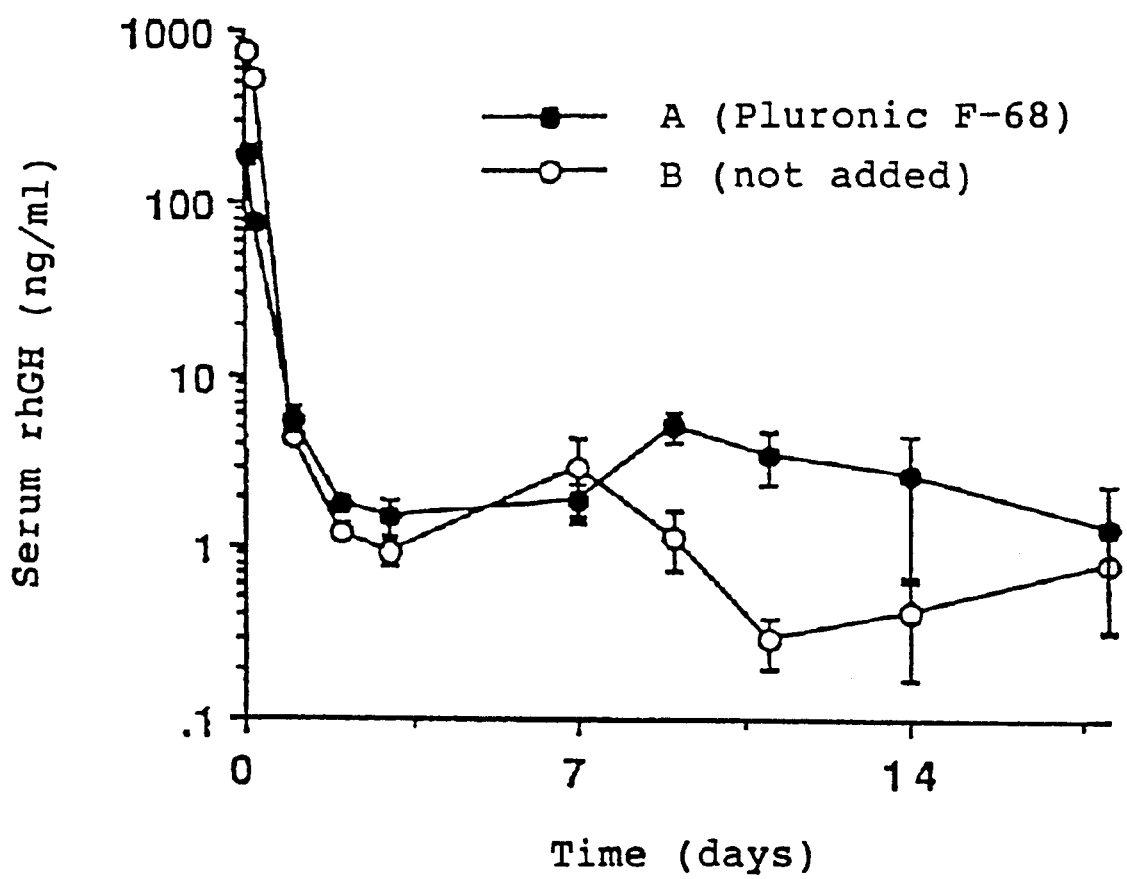
FIG. 1 shows the results of Test Example 1 wherein the two kinds of microcapsules obtained in accordance with Example 1 and Comparative Example 1 were subcutaneously administered to SD rats and change in the rhGH concentration in the serum with the lapse of time was examined.

Abbreviations for amino acids, peptides and others used in the present specification are based on abbreviations specified by the IUPAC-IUB Commission on Biochemical Nomenclature or abbreviations in common use in relevant fields. When an optical isomer may be present in amino acid, it is of the L-configuration, unless otherwise stated.

The bioactive polypeptide as a component of the present invention is exemplified by various peptides or proteins that possess bioactivity beneficial to mammals and that can be used clinically. Said "bioactive polypeptide" normally has a molecular weight of, for example, about 2,000 to about 200,000, calculated on a monomer basis, preferably about 5,000 to about 50,000, and more preferably about 5,500 to about 30,000. Preferred bioactive polypeptides include polymers classified in the biochemical field as proteins having higher structure. Any kind of bioactive polypeptide can be used for the present invention, as long as the objective of the present invention is accomplished, typical examples including growth factors, hormones, cytokines and enzymes. More specifically, the following polymeric peptides and proteins may be mentioned as examples.

(1) Example growth factors include nerve growth factors (NGF-1, NGF-2 etc.), nerve trophic factor (NTF), epithelial growth factor (EGF), platelet-derived growth factor (PDGF), insulin-like growth factors (IGF-1, IGF-2, IGF-3 etc.), fibroblast growth factors (aFGF, bFGF), osteogen growth factors (BMP-1, BMP-2, BMP-3, BMP-4 etc.), atrial natriuretic factor (ANP) and cartilage induction factor.

(2) Example cytokines include interferons (IFN-α, β, γ etc.), interleukins (IL-1 through IL-11 etc.), cachectin, oncostatin, colony-stimulating factors (G-, M-, GM-CSF etc.), thrombopoietin (TPO) and erythropoietin (EPO).

(3) Example enzymes include tissue plasminogen activator (tPA), urokinase (UK), streptokinase, protein C, metalloproteases, superoxide disumutase (SOD), and factors VIII and IX.

(4) Example hormones include growth hormone (GH), growth hormone-releasing factor (GRF), insulin, glucagon, gastrin, prolactin, adrenocorticotrophic hormone (ACTH), thyroid-stimulating hormone (TSH), follicle-stimulating hormone (FSH), luteinizing hormone (LH), human chorionic gonadotropin (hCG) and calcitonin.

The bioactive polypeptide for the present invention is preferably one having a level of water solubility, the water solubility at 20° C. being over about 1 mg/100 ml, preferably over about 100 mg/100 ml.

Preferable examples of said "bioactive polypeptide" include hormones (e.g., growth hormones, insulins) and cytokines (e.g., interferons, interleukins).

The bioactive polypeptide for the present invention include those naturally derived or those produced by gene recombination (e.g. recombinant human growth hormones (hereinafter referred to briefly as rhGH)). Such bioactive polypeptides may have a sugar chain or not, and may have a number of sugar chains of different structures. Also, they include muteins, derivatives, analogues-and active fragments. The terms "bioactive polypeptides", "growth hormones", "insulins", "interferons", "interleukins" etc. as used below are to be understood to include respectively their muteins, derivatives, analogues, active fragments and those having a sugar chain.

The bioactive polypeptide for the present invention may be in a form of a metal salt and, as long as it is a metal salt that does not adversely affect the living body, any metal salt may be used without limitation. For example, such a metal salt may be a metal salt of a bioactive polypeptide with a water-soluble polyvalent metal salt. The polyvalent metal in said "water-soluble polyvalent metal salt" is exemplified by alkaline earth metals (e.g., calcium, magnesium), zinc (II), iron (II, III), copper (II), tin (II, IV) and aluminum (II, III), zinc, calcium etc. being commonly used. Said "water-soluble polyvalent metal" is exemplified by salts formed between polyvalent metals and acids, e.g., salts of polyvalent metals and inorganic acids, and salts of polyvalent metals and organic acids. Said "salt of polyvalent metal and acid" is preferably a salt having a water solubility of not lower than about 20 mg/ml at normal temperature (20° C.), more preferably not lower than about 100 mg/ml, a salt having a solubility of not lower than about 200 mg/ml being commonly used. The organic acid in said "salt of polyvalent metal and inorganic acid" is exemplified by hydrochloric acid, sulfuric acid, nitric acid and thiocyanic acid. The organic acid in said "salt of polyvalent metal and organic acid" is exemplified by aliphatic carboxylic acids and aromatic acids. Said "aliphatic carboxylic acid" is exemplified by aliphatic carboxylic acids having 2 to 9 carbon atoms (e.g., aliphatic monocarboxylic acids, aliphatic dicarboxylic acids, aliphatic tricarboxylic acids). These aliphatic carboxylic acids may be saturated or unsaturated. Examples of said "aliphatic monocarboxylic acid" include saturated aliphatic monocarboxylic acids having 2 to 9 carbon atoms (e.g., acetic acid, propionic acid, butyric acid, valeric acid, caproic acid, enanthic acid, caprylic acid, pelargonic acid, caprynic acid) and unsaturated aliphatic monocarboxylic acids having 2 to 9 carbon atoms (e.g., acrylic acid, propiolic acid, methacrylic acid, crotonic acid, isocrotonic acid). Examples of said "aliphatic dicarboxylic acid" include saturated aliphatic dicarboxylic acids having 2 to 9 carbon atoms (e.g., malonic acid, succinic acid, glutaric acid, adipic acid, pimelic acid) and unsaturated aliphatic dicarboxylic acids having 2 to 9 carbon atoms (e.g., maleic acid, fumaric acid, citraconic acid, mesaconic acid). Examples of said "aliphatic tricarboxylic acid" include saturated aliphatic tricarboxylic acids having 2 to 9 carbon atoms (e.g., tricarballylic acid, 1,2,3-butanetricarboxylic acid). Said "aliphatic carboxylic acid" may have 1 or 2 hydroxyl groups. Such aliphatic carboxylic acids include glycolic acid, lactic acid, glyceric acid, tartronic acid, malic acid, tartaric acid and citric acid. Said "aliphatic carboxylic acid" is preferably an aliphatic monocarboxylic acid, more preferably an aliphatic monocarboxylic acid having 2 to 9 carbon atoms, acetic acid etc. being commonly used. Examples of said "aromatic acid" include benzoic acid and salicylic acid, benzoic acid being commonly used. Examples of salts of polyvalent metals and inorganic acids, i.e., inorganic acid polyvalent metal salts, include halides (e.g., zinc chloride, calcium chloride), sulfates, nitrates and thiocyanates. Examples of salts of polyvalent metals and aliphatic carboxylic acids, i.e., aliphatic carboxylic acid polyvalent metal salts, include calcium acetate, zinc acetate, calcium propionate, zinc glycolate, calcium lactate, zinc lactate and zinc tartrate. For example, calcium acetate, zinc acetate etc. are preferred, especially zinc acetate being commonly used. Examples of salts of polyvalent metals and aromatic acids, i.e., aromatic acid polyvalent metal salts, include benzoates and salicylates, especially zinc benzoate being commonly used.

The bioactive polypeptide for the present invention is added to an oil phase after being brought into contact with a surfactant. By previously mixing the surfactant and the bioactive polypeptide, the bioactive polypeptide is converted to fine particles that retain its bioactivity within a clinically useful range, e.g., at least 50%, and that is stable, resulting in markedly improved dispersibility in the oil phase. A sustained-release preparation of high ratio of entrapment of the drug, suppressed initial release following administration and constant release rate is thus obtained. Examples of said "oil phase" include organic solvent phases containing a biocompatible polymer.

Although said "surfactant" may be ionic or non-ionic, a nonionic surfactant is preferred. Especially, preferred are nonionic surfactants having a hydrophile-lipophile balance (HLB) of not less 10 (preferably 12–30). Such surfactants include polyoxyethylene-polyoxypropylene copolymers [Poloxamers (Asahi Denka Kogyo): Pluronic F-68, F-87, F-108, F-127, L-44 etc.], polyoxyethylene sorbitan fatty acid esters [polysorbates (Nikko Chemicals): Tween 80, 60, 40, 20 etc.], polyoxyethylene hydrogenated castor oils [Nikko Chemicals: HCO-60, -50, -40 etc.], polyoxyethylene alkyl ethers [Nikko chemicals: polyoxyethylene lauryl ether etc.], sorbitan fatty acid esters [Spans (Nikko Chemicals): Span 80, 60, 40, 20, sesquioleic acid sorbitan etc.], sucrose fatty acid esters [DK esters (Daiichi Kogyo); SS, F50, F10 etc.], polyvinyl alcohols, and polyvinylpyrrolidones. Preference is given to polyoxyethylene-polyoxypropylene copolymers, polyoxyethylene hydrogenated castor oils, polyoxyethylene alkyl ethers and polyvinyl pyrrodidones. Especially, polyoxyethylene-polyoxypropylene copolymers such as Poloxamers (e.g., Pluronic F-68) etc. are commonly used. These non-ionic surfactants may be used in a mixture of two or more kinds as appropriate to obtain an appropriate hydrophile-lipophile balance (HLB). When two or more kinds of non-ionic surfactants are used, the HLB is preferably not less than 10 (preferably 12 to 30).

The organic solvent used in said "oil phase" may be any one, as long as its boiling point is not higher than 120° C., that is immiscible in water, and that dissolves the high molecular polymer. Specifically, such organic solvents include hydrocarbon halides (e.g., dichloromethane, chloroform, carbon tetrachloride), fatty acid esters (e.g., ethyl acetate, butyl acetate), ethers (e.g., ethyl ether, isopropyl ether), and aromatic hydrocarbons (e.g., benzene, toluene, xylene). These may be used in a mixture of two or more kinds at any ratio.

Mixing of a surfactant and a bioactive polypeptide is normally conducted in an aqueous solution of the bioactive polypeptide. In this case, the aqueous solution may contain water-soluble components, including pH regulators (e.g., ammonium carbonate, sodium hydrogen carbonate, sodium phosphate, acetic acid, hydrochloric acid, sodium hydroxide), stabilizers (e.g., serum albumin, gelatin), preservatives (e.g., para-oxybenzoic acids), salts (e.g., sodium chloride), saccharides (e.g., mannitol, trehalose, dextrose), and amino acids (e.g., glycine, alanine). The ratio of the surfactant to the bioactive polypeptide is not subject to limitation, as long as the bioactivity of the bioactive polypeptide is adjudged clinically useful (e.g., not lower than 50%). For example, the ratio by weight of bioactive polypeptide and surfactant when they are mixed in water is about 1:0.001 to about 1:1,000, preferably about 1:0.01 to about 1:50, and more preferably about 1:0.05 to about 1:20. Also, the amount of surfactant used to the total amount of biodegradable polymer, bioactive polypeptide and surfactant during production of the sustained-release preparation of the present invention is generally about 0.002% (w/w) to about 50% (w/w), preferably about 0.05% (w/w) to about 20% (w/w).

Said "rapidly dried product" means a preparation obtained by drying rapidly a mixture containing a bioactive polypeptide and a surfactant and the method for rapid drying include, for example, freeze drying, spray drying, vacuum drying or a combination thereof. Rapid drying is not subject to limitation regarding conditions, as long as the bioactivity of the bioactive polypeptide in the mixture is retained within a clinically useful range (e.g., not lower than 50%), and as long as the average particle diameter of the rapidly dried product dispersed in the oil phase is about 0.05 $\mu$m to about 50 $\mu$m, preferably about 0.1 $\mu$m to about 30 $\mu$m, more preferably about 0.1 $\mu$m to about 10 $\mu$m, but it is preferably conducted within a temperature range that does not inactivate the bioactive polypeptide due to thermal denaturation.

Said "biocompatible polymer" may be any one without limitation, as long as it becomes compatible with living body tissue and causes no deleterious reaction etc. to the living body after administration to the living body. For example, a biocompatible polymer that is metabolically decomposed in the living body and finally excreted from the body is preferred. Of such biocompatible polymers, high molecular polymers insoluble or sparingly soluble in water are commonly used. Examples of such biocompatible polymers include fatty acid polyesters (e.g., polymers, copolymers or mixtures thereof synthesized from one or more α-hydroxycarboxylic acids (e.g., glycolic acid, lactic acid, hydroxybutyric acid), hydroxydicarboxylic acids (e.g., malic acid), hydroxytricarboxylic acids (e.g., citric acid)], poly-α-cyanoacrylic acid esters and polyamino acids (e.g., poly-γ-benzyl-L-glutamic acid). These may be used in a mixture at any ratio. The type of polymerization may be random, block or graft. Commonly used biodegradable polymers are fatty acid polyesters [e.g., polymers, copolymers or mixtures thereof synthesized from one or more α-hydroxycarboxylic acids (e.g., glycolic acid, lactic acid, hydroxybutyric acid), hydroxydicarboxylic acids (e.g., malic acid), hydroxytricarboxylic acids (e.g., citric acid) and others].

Of the above-mentioned fatty acid polyesters, homopolymers and copolymers (hereinafter sometimes referred to briefly as copolymers including homopolymers and copolymers) synthesized from one or more α-hydroxycarboxylic acids (e.g., glycolic acid, lactic acid, hydroxybutyric acid) are preferred from the viewpoint of biodegradability and biocompatibility. Also, these polymers including homopolymers and copolymers may be used in a mixture at any ratio.

The biocompatible polymer for the present invention is produced by a known method. Although the above-described α-hydroxycarboxylic acid may be of the D- or L-configuration or a mixture thereof, the ratio of the D-/L-configuration (mol/mol %) preferably falls within the range from about 75/25 to about 25/75. α-hydroxy carboxylic acids whose ratio of the D-/L-configuration (mol/mol %) falls within the range from about 60/40 to about 30/70 is commonly used. Example polymers including homopolymers and copolymers (hereinafter referred to briefly as copolymers) of the above-described α-hydroxycarboxylic acids include copolymers of glycolic acid and other α-hydroxy carboxylic acids. Preferably examples of said "α-hydroxy carboxylic acid" include lactic acid and 2-hydroxybutyric acid. Examples of preferable copolymers of a-hydroxycarboxylic acids include lactic acid-glycolic acid copolymer and 2-hydroxybutyric acid-glycolic acid copolymer, especially, lactic acid-glycolic acid copolymer being commonly used. Although the content ratio (lactic acid/glycolic acid) (mol/mol %) of said "lactic acid-glycolic acid copolymer" is not subject to limitation, as long as the objective of the present invention is accomplished, it is normally about 100/0 to about 30/70. Said content ratio is preferably about 90/10 to about 40/60, those having a content ratio of about 80/20 to about 45/55 being commonly used. Said "lactic acid-glycolic acid copolymer" has a weight-average molecular weight of about 3,000 to about 70,000, for example. Preferred is a lactic acid-glycolic acid copolymer whose weight-average molecular weight is about 3,000 to about 20,000, those having a weight-average molecular weight of about 5,000 to 15,000 being commonly used. Also, the degree of dispersion of said "lactic acid-glycolic acid copolymer" is preferably about 1.2 to about 4.0, those having a degree of dispersion of about 1.5 to about 3.5 being commonly used. Said "lactic acid-glycolic acid copolymer" can be synthesized by a known method, such as that described in Japanese Patent Unexamined Publication No. 28521/1986. Said copolymer is preferably synthesized by catalyst-free dehydration polymerization condensation.

Although said "2-hydroxybutyric acid-glycolic acid copolymer" is not subject to limitation, as long as the objective of the present invention is accomplished, it is preferable that glycolic acid account for about 10 to about 75 mol % and 2-hydroxybutyric acid for the remaining portion. More preferably, glycolic acid accounts for about 20 mol % to about 75 mol %, still more preferably about 30 mol % to about 70 mol %. The weight-average molecular weight of said "2-hydroxybutyric acid-glycolic acid copolymer" is preferably about 2,000 to about 20,000. The degree of dispersion of said "2-hydroxybutyric acid-glycolic acid copolymer" (weight-average molecular weight/number-average molecular weight) is preferably about 1.2 to 4.0, more preferably about 1.5 to 3.5. Said "2-hydroxybutyric acid-glycolic acid copolymer" can be produced by a commonly known process, such as that described in Japanese Patent Unexamined Publication No. 28521/1986. It is preferable that said copolymer be synthesized by catalyst-free dehydration polymerization condensation.

Although said "a-hydroxycarboxylic acid" is not subject to limitation, as long as the objective of the present invention is accomplished, lactic acid polymers may be mentioned as preferable examples of its polymer. The weight-average molecular weight of said "lactic acid polymer, i.e. polylactic acid" is preferably about 3,000 to about 20,000, more preferably about 5,000 to about 15,000. Said "polylactic acid" can be produced by a commonly known process, such as that described in Japanese Patent Unexamined Publication No. 28521/1986. It is preferable that said polymer be synthesized by catalyst-free dehydration polymerization condensation.

Said "2-hydroxybutyric acid-glycolic acid copolymer" may be used in a mixture with a polylactic acid. Although said "polylactic acid" may be of the D- or L-configuration or a mixture thereof, the ratio of the D-/L-configuration (mol/mol %) falls within the range from about 75/25 to about 20/80, for example. Preferred is a polylactic acid whose ratio of the D-/L-configuration (mol/mol %) is about 60/40 to about 25/75, with greater preference given to a polylactic acid whose ratio of the D-/L-configuration (mol/mol %) is about 55/45 to about 25/75. Said "polylactic acid" has a weight-average molecular weight of about 1,500 to about 20,000, for example. Preferred is a polylactic acid whose weight-average molecular weight is about 1,500 to about 10,000. Also, the degree of dispersion of said "polylactic acid" is about 1.2 to about 4.0, preferably about 1.5 to about 3.5. For producing said "polylactic acid," some methods are known, including ring-opening polymerization of lactide, a dimer of lactic acid, and dehydration polycondensation of lactic acid. For obtaining a polylactic acid of relatively low molecular weight for the present invention, direct dehydration polycondensation of lactic acid as described in, for example, Japanese Patent Unexamined Publication No. 28521/1986, is preferred.

When a 2-hydroxybutyric acid-glycolic acid copolymer and polylactic acid are used in a mixture, their mixing ratio is about 10/90 to about 90/10 (% by weight), for example. The mixing ratio is preferably about 20/80 to about 80/20, more preferably about 30/70 to about 70/30.

In the present specification, weight-average molecular weight is defined as the molecular weight based on polystyrene obtained by gel permeation chromatography (GPC) with 9 polystyrenes as reference substances with respective weight-average molecular weights of 120,000, 52,000, 22,000, 9,200, 5,050, 2,950, 1,050, 580 and 162. Number-average molecular weight is also calculated by GPC measurement. Degree of dispersion is calculated from weight-average molecular weight and number-average molecular weight. GPC measurements were taken using a GPC column KF804Lx2 (produced by Showa Denko) and an RI monitor L-3300 (produced by Hitachi, Ltd.) with chloroform as the mobile phase.

The biocompatible polymer for the present invention may be used as a metal salt. The metal salt used to convert said "biocompatible polymer" into a metal salt thereof may be any one without limitation, as long as it is a metal salt that does not adversely affect the living body. Said "metal salt" is exemplified by salts formed between monovalent or polyvalent metals and inorganic or organic acids. Said "monovalent metal" is exemplified by alkali metals (e.g., sodium, potassium). Said "polyvalent metal" is exemplified by alkaline earth metals (e.g., calcium, magnesium), zinc (II), iron (II, III), copper (II), tin (II, IV) and aluminum (II, III). Said "metal" is preferably a polyvalent metal. More preferred are alkaline earth metals and zinc, especially calcium, zinc etc. being commonly used. Said "inorganic acid" is exemplified by hydrochloric acid, hydrobromic acid, hydroiodic acid, hydrofluoric acid, sulfuric acid, nitric acid and thiocyanic acid. Said "organic acid" is exemplified by aliphatic carboxylic acids and aromatic acids. Said "aliphatic carboxylic acid" is exemplified by aliphatic carboxylic acids having 1 to 9 carbon atoms (e.g., aliphatic monocarboxylic acids, aliphatic dicarboxylic acids, aliphatic tricarboxylic acids). Said "aliphatic carboxylic acid" may be saturated or unsaturated. Examples of said "aliphatic monocarboxylic acid" include saturated aliphatic monocarboxylic acids having 1 to 9 carbon atoms (e.g., carbonic acid, acetic acid, propionic acid, butyric acid, valeric acid, caproic acid, enanthic acid, caprylic acid, pelargonic acid, caprynic acid) and unsaturated aliphatic monocarboxylic acids having 2 to 9 carbon atoms (e.g., acrylic acid, propiolic acid, methacrylic acid, crotonic acid, isocrotonic acid). Examples of said "aliphatic dicarboxylic acid" include saturated aliphatic dicarboxylic acids having 2 to 9 carbon atoms (e.g., malonic acid, succinic acid, glutaric acid, adipic acid, pimelic acid) and unsaturated aliphatic dicarboxylic acids having 2 to 9 carbon atoms (e.g., maleic acid, fumaric acid, citraconic acid, mesaconic acid). Examples of said "aliphatic tricarboxylic acid" include saturated aliphatic tricarboxylic acids having 2 to 9 carbon atoms (e.g., tricarballylic acid, 1,2,3-butanetricarboxylic acid). Said "aliphatic carboxylic acid" may have 1 or 2 hydroxyl groups. Such aliphatic carboxylic acids include glycolic acid, lactic acid, glyceric acid, tartronic acid, malic acid, tartaric acid and citric acid. Said "aliphatic carboxylic acid" is preferably an aliphatic monocarboxylic acid, more preferably an aliphatic monocarboxylic acid having 2 to 9 carbon atoms, acetic acid etc. being commonly used. Said "aromatic acid" is exemplified by benzoic acid, salicylic acid and phenolsulfonic acid. The metal salt used to convert the biocompatible polymer into a metal salt is preferably a salt formed between a polyvalent metal and an inorganic or organic acid (hereinafter referred to as polyvalent metal salt). Said "polyvalent metal salt" is exemplified by zinc salts with inorganic acids [e.g., zinc halides (e.g., zinc chloride, zinc bromide, zinc iodide, zinc fluoride), zinc sulfate, zinc nitrate, zinc thiocyanate], zinc salts with organic acids [e.g., aliphatic carboxylic acid zinc salts (e.g., zinc carbonate, zinc acetate, zinc glycolate, zinc lactate, zinc tartrate), aromatic acid zinc salts (e.g., zinc benzoate, zinc salicylate, zinc phenolsulfonate)], calcium salts with inorganic acids [e.g., calcium halides (e.g., calcium chloride, calcium bromide, calcium iodide, calcium fluoride), calcium sulfate, calcium nitrate, calcium thiocyanate], and calcium salts with organic acids [e.g., aliphatic carboxylic acid calcium salts (e.g., calcium carbonate, calcium acetate, calcium propionate, calcium oxalate, calcium tartrate, calcium lactate, calcium citrate, calcium gluconate), aromatic acid calcium salts (e.g., calcium benzoate, calcium salicylate)]. Of these examples of said "polyvalent metal salts", zinc acetate, calcium acetate etc. are commonly used.

The sustained-release preparation of the present invention is prepared by dispersing a solid or semi-solid component obtained by mixing a bioactive polypeptide and a surfactant in an oil phase containing a biocompatible polymer. When a bioactive polypeptide and a surfactant are mixed, a rapidly dried product obtained by rapidly drying a mixture (e.g., aqueous solution or suspension preferred) containing them. Because the rapidly dried product of the present invention is preferably uniformly dispersed in an oil phase in the form of finer particles after being dispersed in the oil phase, it is preferable that it be subjected to ultrasonic irradiation, particle size reduction using a homogenizer, or the like. Said "sustained-release preparation" can be produced by, for example, the aqueous drying method, phase separation method, spray drying method and methods based thereon.

Some production methods for sustained-release preparations in the form of, for example, microcapsules, are described below.

(a) In-water drying method (s/o/w method)

In this method, a bioactive polypeptide and a surfactant are first mixed and subsequently subjected to rapid drying (e.g., freeze-drying, vacuum drying) to yield a rapidly dried product. In the meantime, an organic solvent solution containing a biocompatible polymer is prepared. The organic solvent used to produce the sustained-release preparation of the present invention preferably has a boiling point not higher than 120° C. Examples of said "organic solvent" include halogenated hydrocarbons (e.g., dichloromethane, chloroform, carbon tetrachloride) and fatty acid esters (e.g., ethyl acetate, butyl acetate). These may be used in combination at appropriate ratios. Said "organic solvent" is preferably dichloromethane, ethyl acetate, or the like, dichloromethane being commonly used. Depending on the molecular weight of the biocompatible polymer, type of the organic solvent and other factors, the biocompatible polymer concentration in the organic solvent solution is normally chosen over the range from about 0.01% (w/w) to about 80% (w/w), preferably about 0.1% (w/w) to about 70% (w/w), those having a biocompatible polymer of about 1% (w/w) to about 60% (w/w) being commonly used.

To the thus-obtained organic solvent solution containing the biocompatible polymer, the above-described rapidly dried product of bioactive polypeptide and surfactant is added and dispersed by homogenization, for example, with use of a vortex mixer. The resulting s/o suspension permits improvement of dispersibility by emulsification using a homogenizer like Polytron (produced by Kinematica), ultrasonication, or the like. This s/o emulsion is then added to an aqueous phase containing an additional surfactant (e.g., polyvinyl alcohol, polyvinylpyrrolidone, carboxymethyl cellulose), and treated using a turbine type mechanical stirrer or the like to yield an s/o/w emulsion, after which the oil phase solvent is evaporated to produce microcapsules. The volume of the aqueous phase is chosen over the range from about 1 to about 10,000 times, preferably about 2 to about 5,000 times, more preferably about 5 to about 2,000 times, the volume of the oil phase. In this case, pH regulators (e.g., acetic acid, hydrochloric acid, sodium hydroxide), stabilizers (e.g., serum albumin, gelatin), preservatives (e.g, para-oxybenzoic acids) and, as osmotic pressure regulators, salts (e.g., sodium chloride), saccharides (e.g., mannitol) etc. may be added to said "aqueous phase."

The microcapsules thus obtained are collected by centrifugation or filtration, after which they are repeatedly washed several times with distilled water to remove the emulsifier etc. adhering to the microcapsule surface, then re-dispersed in distilled water etc., with the addition of mannitol etc. as necessary, followed by freeze drying. The water and organic solvent in the microcapsules are then removed by heating under reduced pressure as necessary. Regarding heating conditions, for example, the microcapsules are heated to a temperature higher by about 5° C. than the intermediate glass transition point of the biocompatible polymer at a rate of 10° to 20° C. per minute, using a differential scanning calorimeter; after the microcapsules have reached a given temperature, constant temperature is maintained for 1 week, preferably for 2 or 3 days, and more preferably for about 1 to 24 hours.

(b) Phase separation method (coacervation method)

In producing microcapsules by this method, a coacervating agent is added little by little to the s/o emulsion of a bioactive polypeptide, a surfactant and a biocompatible polymer described in term (a) above during stirring, to separate and solidify the microcapsules. Said "coacervating agent" is added in an amount by volume of about 0.01 to about 2,000 times, preferably about 0.05 to about 500 times, and more preferably about 0.1 to about 200 times, the volume of the emulsion. Said "coacervating agent" may be any one, as long as it is a polymer, a mineral oil or a vegetable oil that is miscible in the organic solvent used as the solvent for the biocompatible polymer and that does not dissolve said "biocompatible polymer." Specifically, useful coacervating agents include silicon oil, sesame oil, soybean oil, corn oil, cotton seed oil, coconut oil, linseed oil, mineral oil, n-hexane and n-heptane. These may be used in combination. The microcapsules thus obtained are collected by centrifugation or filtration, after which they are repeatedly washed with heptane etc. to remove the coacervating agent. The microcapsules are then washed in the same manner as in term (a) above and then freeze-dried.

In microcapsule production by said "in-water drying method" or "phase separation method," an anticoagulant or antiflocculant (hereinafter referred to as anticoagulant) may be added to prevent particle aggregation. Said "anticoagulant" is exemplified by water-soluble polysaccharides such as mannitol, lactose, glucose, starches (e.g., corn starch), hyaluronic acid or alkali metal salts thereof; proteins such as fibrinogen and collagen; and inorganic salts such as sodium chloride and sodium hydrogen phosphate.

(c) Spray drying method

In producing microcapsules by this method, an s/o emulsion containing a bioactive polypeptide, a surfactant and a biocompatible polymer described in term (a) above is sprayed via a nozzle into the drying chamber of a spray drier to volatilize the organic solvent in the fine droplets in a very short time, to yield fine particles. Said "nozzle" is exemplified by the double-fluid nozzle, pressure nozzle and rotary disc nozzle. To prevent aggregation on coagulation where desired, the anticoagulant described in term (b) above may be sprayed via another nozzle. The microcapsules thus obtained may have the water and organic solvent removed at increased temperature under reduced pressure in the same manner as in term (a) above, when necessary.

The sustained-release preparation of the present invention can be administered as above-obtained microcapsules as such or in the form of various dosage forms prepared from these microcapsules as a starting material, e.g., non-oral preparations (e.g., intramuscular, subcutaneous, visceral, periosteal or articular injections or indwellable preparations, nasal, rectal or uterine transmucosal preparations) and oral preparations [e.g., capsules (e.g., hard capsules, soft capsules), solid preparations such as granules and powders, liquid preparations such as suspensions].

The sustained-release preparation of the present invention is preferably an injectable preparation. When the microcapsules obtained by one of the above-described methods are applied for an injectable preparation, they can be prepared as a sustained-release injectable preparation by suspending microcapsules in water, along with a dispersing agent (e.g., surfactants such as Tween 80 and HCO-60, polysaccharides such as carboxymethyl cellulose, sodium alginate and sodium hyaluronate, protamine sulfate, polyethylene glycol 400), a preservative (e.g., methyl paraben, propyl paraben), an isotonizing agent (e.g., sodium chloride, mannitol, sorbitol, glucose), a local anesthetizing agent (e.g., xylocaine hydrochloride, chlorobutanol) etc., to yield an aqueous suspension, or by dispersing it in a vegetable oil such as sesame oil or corn oil with or without a phospholipid such as lecithin or a moderate-chain fatty acid triglyceride (e.g., MIGLYOL 812), to yield an oily suspension.

When the sustained-release preparation is a microcapsule, for example, it is particularly preferable that it be in a fine particle form. When the microcapsule is used as an injectable suspension, its average particle diameter is chosen over the range from about 0.1 $\mu$m to 300 $\mu$m, for instance, as long as the requirements concerning the degree of dispersion and needle passage are met. Preferably, said "fine particles" have an average particle diameter of about 1 $\mu$m to 200 $\mu$m, those having a particle diameter falling within the range from about 2 $\mu$m to 100 $\mu$m being commonly used.

The above-described microcapsule can be prepared as a sterile preparation without limitation by the method in which the entire production process is sterile, the method in which gamma rays are used as sterilant, and the method in which an antiseptic is added.

With low toxicity, the sustained-release preparation of the present invention can be safely used in mammals (e.g., humans, bovines, swines, dogs, cats, mice, rats, rabbits).

Indications for the sustained-release preparation of the present invention vary according to the bioactive polypeptide used. For example, the sustained-release preparation of the present invention is effective in the treatment or prevention of diabetes mellitus etc. when said "bioactive polypeptide" is an insulin; growth hormone deficiency, Turner's syndrome, pituitary drawfism, chronic renal disease, achondroplasia, adult hypopituitarism, Down syndrome, Silver syndrome, hypochondroplasia, osteoporosis, juvenile chronic arthritis, etc. when the bioactive polypeptide is a growth hormone; viral hepatitis (e.g., hepatitis C, HBe antigen positive active hepatitis), cancers (e.g., renal cancer, multiple myeloma) etc. when the bioactive polypeptide is an interferon-a; anemia (e.g., anemia during renal dialysis) etc. when the bioactive polypeptide is an erythropoietin or a thrombopoietin; neutropenia (e.g., during anticancer agent therapy), infectious diseases etc. when the bioactive polypeptide is G-CSF; cancers (e.g., hemangioendothelioma, renal cancer) etc. when the bioactive polypeptide is an IL-2; digestive ulcers etc. when the bioactive polypeptide is a FGF; thrombocytopenia etc. when the bioactive polypeptide is FGF-9; senile dementia, neuropathy etc. when the bioactive polypeptide is a NGF; thrombosis etc. when the bioactive polypeptide is a tPA, and cancers etc. when the bioactive polypeptide is a tumor necrosis factor.

Depending on the type and content of the bioactive polypeptide, duration of release, target disease, subject animal and other factors, the dose of the sustained-release preparation may be set at any level, as long as an effective concentration of said "bioactive polypeptide" is retained in the body. The dose per administration of said "bioactive polypeptide" may be chosen as appropriate over the range from about 0.0001 mg/kg to 10 mg/kg body weight for each adult, when the preparation is a 1-week preparation. More preferably, the dose may be chosen as appropriate over the range from about 0.0005 mg/kg to 1 mg/kg body weight. Dosing frequency may be chosen as appropriate, e.g., once weekly, once every two weeks, or once monthly, depending on type, content and dosage form of said "bioactive polypeptide," duration of release, subject disease, subject animal and other factors.

For administration to a patient with pituitary dwarfism, a 2-week sustained preparation whose active ingredient is human growth hormone, for example, is normally administered at a dose chosen as appropriate over the range from about 0.01 mg/kg to about 5 mg/kg body weight, preferably about 0.03 mg/kg to about 1 mg/kg body weight, based on the active ingredient, preferably once every two weeks. When the bioactive polypeptide is insulin, the dose for a diabetic patient is normally chosen over the range from about 0.001 to about 1 mg/kg body weight, preferably about 0.01 to about 0.2 mg/kg, preferably once weekly.

Although the preparation of the present invention may be stored at normal temperature or in a cold place, it is preferable to store it in a cold place. Normal temperature and a cold place mentioned herein are as defined by the Pharmacopoeia of Japan; specifically, 15° to 25° C. for normal temperatures and under 15° C. for cold places.

The sustained-release preparation of the present invention is advantageous in that initial release is suppressed to ensure a constant release rate over an extended period of time by mixing a bioactive polypeptide and a surfactant, followed by rapid drying, uniformly dispersing the rapidly dried product in an oil phase, and subsequently shaping the dispersion into a sustained-release preparation.

EXAMPLE 1

After 60 mg of recombinant human growth hormone (rhGH) and 20 mg of Pluronic F-68 were dissolved in 6 ml of distilled water, the solution was freeze-dried. The resulting powder was dispersed in a solution of 1,920 mg of a lactic acid-glycolic acid copolymer (lactic acid/glycolic acid=75/25; average molecular weight 8,400, based on polystyrene) in 2.5 ml of methylene chloride, and subjected to size reduction using Polytron, after which it was prepared as an s/o/w emulsion in 800 ml of a 0.1% aqueous solution of PVA being cooled at 15° C. using a homogenizer. This emulsion was then gradually stirred for 3 hours using an ordinary propeller type mechanical stirrer. After solidification with methylene chloride volatilization, microcapsules were collected using a centrifuge and simultaneously washed with purified water. The collected microcapsules were freeze-dried for one day to yield a powder.

COMPARATIVE EXAMPLE 1

After 60 mg of rhGH was dissolved in 6 ml of distilled water, the solution was freeze-dried. The resulting powder was dispersed in a solution of 1,940 mg of a lactic acid-glycolic acid copolymer (lactic acid/glycolic acid=75/25; average molecular weight 8,400, based on polystyrene) in 2.5 ml of methylene chloride, and subjected to size reduction using Polytron, after which it was prepared as an s/o/w emulsion in 800 ml of a 0.1% aqueous solution of PVA being cooled at 15° C. using a homogenizer. The same procedure as the method of Example 1 was then followed to yield a microcapsule powder. Table 1 shows the characteristics of the microcapsules obtained by the methods of Example 1 and Comparative Example 1.

TABLE 1

| Production Method | Surfactant | rhGH Entrapment Ratio | Release Percentage during the first 1 day (in vitro Release Test) |
|---|---|---|---|
| Example 1 | Pluronic F-68 | 105% | 38% |
| Comparative Example 1 | Not added | 63% | 68% |

From the results in Table 1, it is evident that the addition of a surfactant (Pluronic F-68) improves rhGH entrapment ratio of microcapsules, and suppresses initial release (one-day release) in the in vitro release test.

COMPARATIVE EXAMPLE 2

After 60 mg of rhGH was dissolved in 6 ml of distilled water, the solution was freeze-dried. The powder obtained was dispersed in a solution of 20 mg of Pluronic F-68 and 1.920mg of a lactic acid-glycolic acid copolymer (lactic acid/glycolic acid=75:25, polystyrene-based average molecular weight 8,400) in 2.5 ml of methylene chloride, and micronized using Polytron. This was then treated in 800 ml of a 0.1% aqueous solution of PVA being cooled to 15°

C., using a homogenizer, to yield an s/o/w emulsion. The same procedure as Example 1 was then followed to yield a microcapsule powder.

Table 2 shows the characteristics of the microcapsules obtained by the methods of Example 1 and Comparative Example 2.

TABLE 2

| Production Method | Surfactant | rhGH Entrapment Ratio | Release Percentage during the first 1 day (in vitro Release Test) |
|---|---|---|---|
| Example 1 | Pluronic F-68 freeze-dried | 105% | 38% |
| Comparative Example 2 | Pluronic F-68 dissolved in oil phase | 69% | 62% |

The results shown in Table 2 demonstrate that the microcapsules prepared by the method of Example 1 using a freeze-dried powder obtained after a surfactant (Pluronic F-68) was added to rhGH exhibited an increased ratio of rhGH entrapment in microcapsules and suppressed initial drug release (daily release) in the in vitro release test, in comparison with those prepared by the method of Comparative Example 2 using an oil phase (dichloromethane) in which the same amount of surfactant was dissolved.

EXAMPLE 2

After 100 mg of rhGH and 100 mg of Pluronic F-68 were dissolved in 20 ml of distilled water, the solution was freeze-dried. The resulting powder was dispersed in a solution of 1,800 mg of a lactic acid-glycolic acid copolymer (lactic acid/glycolic acid=50/50; average molecular weight 10,100, based on polystyrene) in 2.5 ml of ethyl acetate, and subjected to size reduction using Polytron, after which it was prepared as an s/o/w emulsion in 800 ml of a 0.5% aqueous solution of PVA being cooled at 15° C. using a homogenizer. This emulsion was then gradually stirred for 3 hours using an ordinary propeller type mechanical stirrer. After solidification with ethyl acetate volatilization, microcapsules were collected using a centrifuge and simultaneously washed with purified water. The collected microcapsules were freeze-dried for one day to yield a powder.

EXAMPLE 3

After 50 mg of rhGH, 50 mg of Pluronic F-68 and 10 mg of HCO-60 were dissolved in 10 ml of distilled water, the solution was freeze-dried. The resulting powder was dispersed in a solution of 1,890 mg of a hydroxybutyric acid-glycolic acid copolymer (hydroxybutyric acid/glycolic acid=75/25; average molecular weight 12,000, based on polystyrene) in 5 ml of methylene chloride, and subjected to size reduction using Polytron, after which it was prepared as an s/o/w emulsion in 1,000 ml of a 0.2% aqueous solution of PVA containing 5% mannitol, being cooled at 15° C., using a homogenizer. This emulsion was then gradually stirred for 3 hours using an ordinary propeller type mechanical stirrer. After solidification with methylene chloride volatilization, microcapsules were collected using a centrifuge and simultaneously washed with purified water. The collected microcapsules were freeze-dried for one day to yield a powder.

EXAMPLE 4

After 10 mg of interferon-a and 30 mg of Pluronic F-68 were dissolved in 10 ml of distilled water, the solution was freeze-dried. The resulting powder was dispersed in a solution of 1,960 mg of a hydroxybutyric acid-glycolic acid copolymer (hydroxybutyric acid/glycolic-acid=75/25; average molecular weight 12,000, based on polystyrene) in 5 ml of methylene chloride, and subjected to size reduction using Polytron, after which it was prepared as an s/o/w emulsion in 1,000 ml of a 0.2% aqueous solution of PVA being cooled at 15° C. using a homogenizer. This emulsion was then gradually stirred for 3 hours using an ordinary propeller type mechanical stirrer. After solidification with methylene chloride volatilization, microcapsules were collected using a centrifuge and simultaneously washed with purified water. The collected microcapsules were freeze-dried for one day to yield a powder.

EXAMPLE 5

To 4.7 ml of an aqueous solution containing 60 mg of rhGH and 2 mg of Pluronic F-68, 0.5 ml of an aqueous solution containing 100 mg of salmon-derived free protamine was added, followed by slow stirring at 25° C. for 20 minutes, to yield an insoluble complex, which was then freeze-dried. The powder obtained was dispersed in a solution of 1,838 mg of a polylactic acid polymer (lactic acid 100%, polystyrene-based average molecular weight 9,000) whose carboxyl group terminal was previously completely ethyl-esterified, in 5 ml of methylene chloride, and micronized using Polytron at 15,000 rpm for 1 minute, then by ultrasonication for 2 minutes. This was then treated in 800 ml of a 0.1% aqueous solution of PVA containing 5% mannitol being cooled to 15° C., using a homogenizer, to yield an s/o/w emulsion. This emulsion was then slowly stirred for 3 hours using an ordinary propeller type mechanical stirrer; after solidification with methylene chloride volatilization, microcapsules were collected using a centrifuge and simultaneously washed with purified water. The collected microcapsules were freeze-dried for one day to yield a powder.

EXAMPLE 6

After 75 mg of rhGH and 15 mg of polyoxyethylene hydrogenated castor oil RCO-60 were dissolved in 15 ml of 5 mM ammonium hydrogen carbonate buffer (pH 7.8), an aqueous solution of zinc acetate (5 mg/ml) was gradually added to yield an insoluble complex (rhGH:Zn=1:7 by molar ratio). After centrifugation, the residue was re-dispersed in a small amount of distilled water and freeze-dried. The powder obtained was dispersed in a solution of 1,425 mg of a lactic acid-glycolic acid copolymer (lactic acid/glycolic acid=50:50, polystyrene-based average molecular weight 15,000) in 2 ml of methylene chloride, and micronized by ultrasonication for 5 minutes, then using Polytron at 15,000 rpm for 1 minute. This was then treated in 800 ml of a 0.1% aqueous solution of PVA containing 10% mannitol being cooled to 15° C., using a homogenizer, to yield an s/o/w emulsion. The same procedure as Example 5 was then followed to yield microcapsules.

EXAMPLE 7

Method A:

After 75 mg of rhGH and 15 mg of Pluronic F-68 were dissolved in 6 ml of distilled water, the solution was freeze-dried. The powder obtained was dispersed in a solution of 1,410 mg of a lactic acid-glycolic acid copolymer (lactic acid/glycolic acid=50:50, polystyrene-based average molecular weight 15,000) in 3 ml of methylene chloride, and mixed using a vortex mixer for about 30 seconds. After 0.1 ml of this s/o dispersion was diluted with methylene chloride, rhGH particle diameter was determined using a laser diffraction particle size distribution analyzer. The above s/o dispersion was treated in 800 ml of a 0.1% aqueous solution of PVA containing 10% mannitol being cooled to 15° C., using a homogenizer, to yield an s/o/w emulsion. The same procedure as Example 5 was then followed to yield microcapsules.

Method B:

After 75 mg of rhGH and 15 mg of Pluronic F-68 were dissolved in 6 ml of distilled water, the solution was freeze-dried.

The powder obtained was dispersed in a solution of 1,410 mg of a lactic acid-glycolic acid copolymer (lactic acid/glycolic acid=50:50, polystyrene-based average molecular weight 15,000) in 3 ml of methylene chloride, and thoroughly micronized by ultrasonication for 5 minutes, then using Polytron at 15,000 rpm for 1 minute. After 0.1 ml of this s/o dispersion was diluted with methylene chloride, rhGH particle diameter was determined using a laser diffraction particle size distribution analyzer. The above s/o dispersion was treated in the same manner as Example 5 to yield microcapsules.

COMPARATIVE EXAMPLE 3

After 75 mg of rhGH was dissolved in 6 ml of distilled water, the solution was freeze-dried. The powder obtained was dispersed in a solution of 1,410 mg of a lactic acid-glycolic acid copolymer (lactic acid/glycolic acid=50:50, polystyrene-based average molecular weight 15,000) in 3 ml of methylene chloride, and mixed using a vortex mixer for about 30 seconds. After 0.1 ml of this s/o dispersion was diluted with methylene chloride, rhGH particle diameter was determined using a laser diffraction particle size distribution analyzer. The above s/o dispersion was treated by the same procedure as Example 7-Method A to yield microcapsules.

Table 3 shows the characteristics of the microcapsules obtained by methods A and B and the method of Comparative Example 3.

TABLE 3

| Method of Production | Mean Particle Diameter of rhGH in s/o Dispersion | rhGH Entrapment Ratio |
|---|---|---|
| Example 7-Method A | 12.1 μm | 97% |
| Example 7-Method B | 6.2 μm | 103% |
| Comparative Example 3 | 40.3 μm | 71% |

The results shown in Table 3 demonstrate that the microcapsules prepared in accordance with the present invention using an s/o dispersion containing rhGH particles not more than 20 μm in mean particle diameter exhibited an increased rhGH entrapment ratio, in comparison with those prepared without rapidly drying rhGH with a surfactant using an s/o dispersion containing rhGH particles not less than 30 μm in mean particle diameter.

Test Example 1

The two kinds of microcapsules obtained in Example 1 and Comparative Example 1 above were each subcutaneously administered to SD rats (male, 6 weeks of age) at 15 mg/kg, and their serum concentrations were measured by radioimmunoassay (Ab beads HGH, Eiken Kagaku). The results are shown in FIG. 1.

By the addition of Pluronic F-68, the rise in serum rhGH concentration as often noted early after administration of s/o/w type microcapsules was suppressed, enabling more stable sustained release of the drug for an extended period of time. As a result, the ratio of AUC (Area Under the concentration) during the first 1 day to AUC during 18 days, an index of initial release in vivo, was suppressed to 56% in the presence of Pluronic F-68, in comparison with 94% in the absence of surfactants.

Test Example 2

Figure 2:
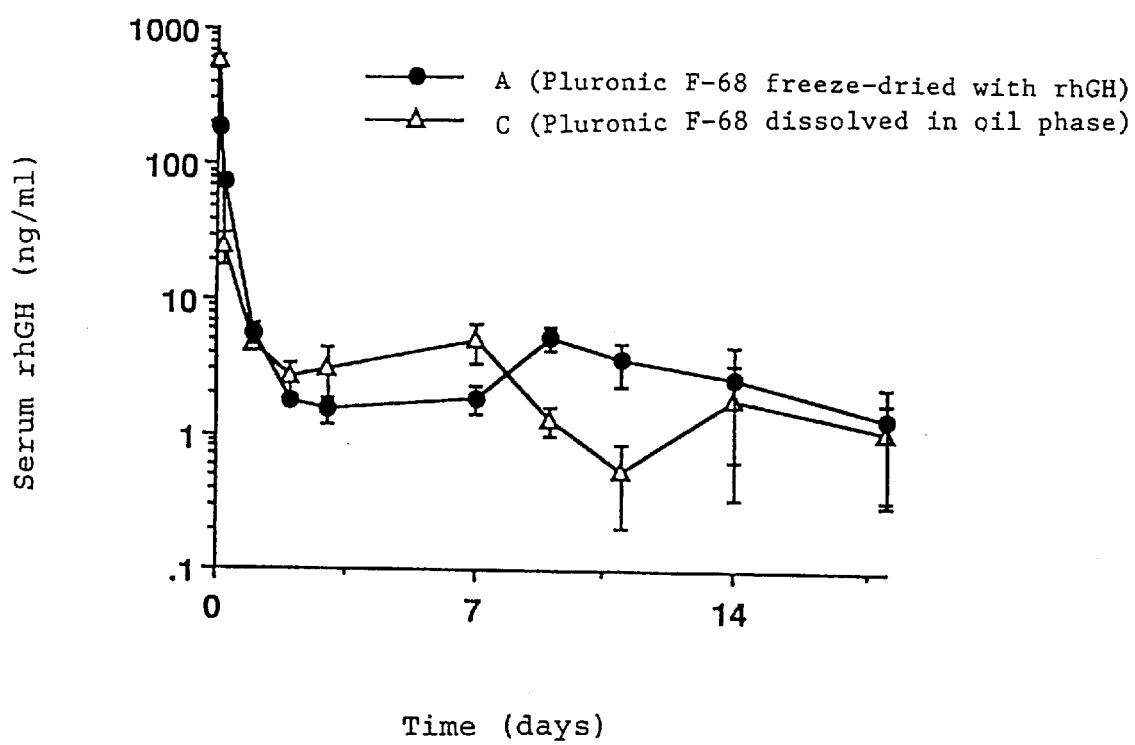
FIG. 2 shows the results of Text Example 2 wherein the two kinds of microcapsules obtained in accordance with Example 1 and Comparative Example 2 were subcutaneously administered to SD rats and change in the rhGH concentration in the serum with the lapse of time was examined.

The two kinds of microcapsules obtained by the methods of Example 1 and that of Comparative Example 2 above were each subcutaneously administered at 15 mg/kg to SD rats (male, 6 weeks of age); their serum concentrations were determined by the radioimmunoassay described in Test Example 1. The results obtained are shown in FIG. 2.

The microcapsules prepared by the method of Example 1 using a freeze-dried powder obtained after Pluronic F-68 was added to rhGH exhibited more stable sustained release, with a lower increase in serum rhGH concentration early after administration, in comparison with those prepared by the method of Comparative Example 2 using an oil phase (dichloromethane) in which the same amount of surfactant was dissolved. As a result, the microcapsules prepared by the method of Example 1 showed 188 ng/ml serum concentration one hour after administration, while those by the method of Comparative Example 2 showed 574 ng/ml. The ratio of AUC for the first 1 day to that for 18 days, an index of initial release in vivo, was suppressed to 56% in the method of Example 1 involving freeze-drying of Pluronic F-68/rhGH, in comparison with 67% in the method of Comparative Example 2 involving Pluronic F-68 addition to the oil phase.

Test Example 3

Figure 3:
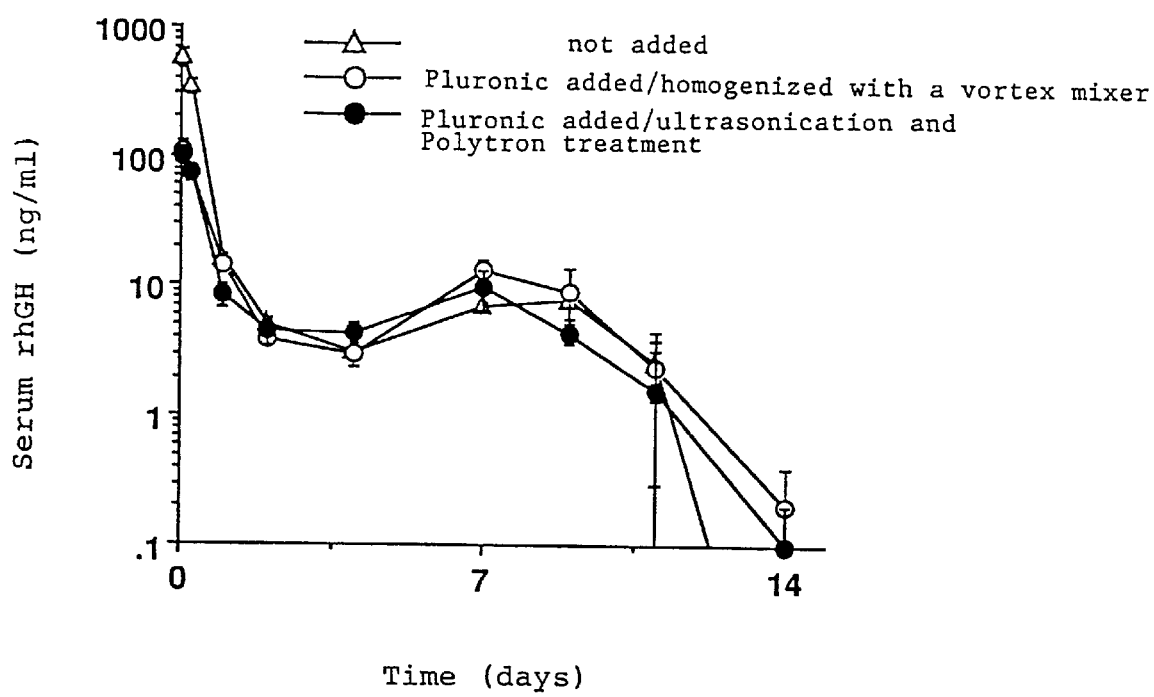
FIG. 3 shows the results of Test Example 3, wherein the three kinds of microcapsules obtained in accordance with methods A and B of Example 7, and the method of Comparative Example 3 were subcutaneously administered to SD rats and change in the rhGH concentration in the serum with the lapse of time was examined.

The three kinds of microcapsules obtained by methods A, B and the method of Comparative Example 3 described above were each subcutaneously administered at 15 mg/kg to SD rats (male, 6 weeks of age); their serum concentrations were determined by the radioimmunoassay described in Test Example 1. The results obtained are shown in FIG. 3.

By the addition of Pluronic F-68, the rise in serum rhGH concentration as often noted early after administration of s/o/w type microcapsules was suppressed, enabling more stable sustained release of the drug for an extended period of time. As a result, the ratio of AUC (Area Under the concentration) during the first 1 day to AUC during 14 days, an index of initial release in vivo, was suppressed to 47% in the presence of Pluronic F-68, by mixing with a vortex mixer and to 49% in the presence of Pluronic F-68 by treatment with ultrasonication/polytron in comparison with 79% in the absence of surfactants.

We claim:

1. A method of producing a sustained-release preparation, which comprises the steps of:

lyophilizing an admixture of a bioactive polypeptide and a non-ionic surfactant to obtain a lyophilized product, wherein said bioactive polypeptide is hormone or cytokine, and the hydrophile/lipophile balance of said non-ionic surfactant is not less than 10;

dispersing said lyophilized product as a solid phase in an oil in water-type emulsion; and there after shaping the resulting dispersion.

2. A method of claim 1, wherein the average diameter of the lyophilized product dispersed in the oil phase is about 0.05 μm to about 50 μm.

3. A method of claim 1 or 2, wherein the ratio by weight of the bioactive polypeptide and the surfactant is about 1:0.001 to about 1:1,000.

4. A method of claim 1, wherein the oil phase is an organic solvent phase containing a biocompatible polymer.

5. A method of claim 4, wherein the biocompatible polymer concentration in the organic solvent is about 0.01% (w/w) to about 80% (w/w).

6. A method of claim 4, wherein the ratio of the surfactant used to the total amount of the bioactive polypeptide, the surfactant and the biocompatible polymer is about 0.002% (w/w) to about 50% (w/w).

7. A method of claim 1, wherein the bioactive polypeptide is soluble in water.

8. A method of claim 1, wherein the bioactive polypeptide is a hormone.

9. A method of claim 8, wherein the hormone is a growth hormone.

10. A method of claim 1, wherein the bioactive polypeptide is a cytokine.

11. A method of claim 10, wherein the cytokine is an interferon.

12. A method of claim 4, wherein the biocompatible polymer is a biodegradable polymer.

13. A method of claim 12, wherein the biodegradable polymer is a fatty acid polyester.

14. A method of claim 13, wherein the fatty acid polyester is a lactic acid-glycolic acid polymer.

15. A method of claim 13, wherein the molecular weight of the lactic acid-glycolic acid polymer is about 3,000 to 70,000 and the lactic acid/glycolic acid content ratio is about 100/0 to about 30/70.

16. A method of claim 13, wherein the fatty acid polyester is a hydroxybutyric acid-glycolic acid polymer.

17. A method of claim 16, wherein the molecular weight of the hydroxybutyric acid-glycolic acid polymer is about 3,000 to about 70,000 and the hydroxybutyric acid/glycolic acid content ratio is about 100/0 to about 40/60.

18. A method of claim 1, wherein the non-ionic surfactant comprises one or more surfactants selected from the group consisting of polyoxyethylene-polyoxypropylene copolymers and polyoxyethylene hydrogenated castor oils.

19. A method of claim 1, wherein the non-ionic surfactant is a polyoxyethylene-polyoxypropylene copolymer.

20. A method of claim 1, wherein the sustained-release preparation is a microcapsule.

21. A method of claim 20, wherein the average particle diameter of the microcapsule is about 1.0 $\mu$m to about 200 $\mu$m.

22. A method of claim 1, wherein the sustained-release preparation is an injectable preparation.

23. An oil in water-type emulsion having an oil phase comprising a lyophilized product of an admixture of a non-ionic surfactant and a bioactive polypeptide selected from the group consisting of hormones and cytokines, said lyophilized product being dispersed in said oil phase, wherein the hydrophile/lipophile balance of said non-ionic surfactant is not less than 10.

24. A dispersion of claim 23, wherein the average particle diameter of the lyophilized product dispersed in the oil phase is about 0.05 $\mu$m to 50 $\mu$m.

25. A composition which is useful as a starting material for preparing a sustained-release preparation, said composition comprising an oil in water-type emulsion having an oil phase comprising a biocompatible polymer, and a lyophilized product of an aqueous solution or suspension comprising an admixture of a non-ionic surfactant and a bioactive polypeptide selected from the group consisting of hormones and cytokines, wherein said lyophilized product is dispersed in said oil phase and the hydrophile/lipophile balance of said non-ionic surfactant is not less than 10.

26. A sustained-release preparation produced by the method of claim 1.

27. A sustained-release preparation of claim 26, wherein the bioactive polypeptide is a growth hormone.

28. A medicament which, when delivered in an effective amount, treats or prevents growth hormone deficiency, Turner's syndrome, pituitary dwarfism, chronic renal disease, achondroplasia, adult hypopituitarism, Down syndrome, Silver syndrome, hypochondroplasia, osteoporosis and juvenile chronic arthritis, and which comprises the sustained-release preparation of claim 27.

29. A method of treating or preventing growth hormone deficiency, Turner's syndrome, pituitary dwarfism, chronic renal disease, achondroplasia, adult hypopituitarism, Down syndrome, Silver syndrome, hypochondroplasia, osteoporosis and juvenile chronic arthritis, in a subject, which comprises administrating to the subject in need an effective amount of the sustained-release preparation of claim 27.

30. A method of claim 1, wherein the non-ionic surfactant is polyoxyethylene hydrogenated castor oil.

31. A method of claim 1, wherein the sustained-release preparation suppresses the initial release of said bioactive polypeptide.

32. A method of claim 1, wherein the sustained-release preparation achieves an entrapment ratio of bioactive polypeptide of at least 97%.

33. A method of claim 1, wherein the sustained-release preparation provides a substantially constant release rate of said bioactive polypeptide.

* * * * *

UNITED STATES PATENT AND TRADEMARK OFFICE
CERTIFICATE OF CORRECTION

PATENT NO.  : 6,190,702 B1
DATED       : February 20, 2001
INVENTOR(S) : Shigeyuki Takada et al.

It is certified that error appears in the above-identified patent and that said Letters Patent is hereby corrected as shown below:

Column 1,
Line 51, "(U.S. Pat. No. 4962091," should read -- (U.S. Pat. No. 4,962,091, --.

Column 3,
Line 59, "Turnerts" should read -- Turner's --.

Column 7,
Line 19, "include," should read -- includes, --.

Column 16,
Line 41, "RCO-60" should read -- HCO-60 --.

Column 18,
Line 59, "there after" should read -- thereafter --.

Signed and Sealed this

Nineteenth Day of March, 2002

Attest:

Attesting Officer

JAMES E. ROGAN
Director of the United States Patent and Trademark Office